(12) United States Patent
Gwenin et al.

(10) Patent No.: US 9,506,921 B2
(45) Date of Patent: Nov. 29, 2016

(54) METHOD FOR DETERMINING EXPOSURE TO MYCOBACTERIA

(75) Inventors: Christopher David Gwenin, Gwynedd (GB); Mark Stephen Baird, Gwynedd (GB)

(73) Assignee: Bangor University, Gwynedd (GB)

( * ) Notice: Subject to any disclaimer, the term of this patent is extended or adjusted under 35 U.S.C. 154(b) by 320 days.

(21) Appl. No.: 14/008,127

(22) PCT Filed: Mar. 30, 2012

(86) PCT No.: PCT/GB2012/050726
§ 371 (c)(1),
(2), (4) Date: Nov. 6, 2013

(87) PCT Pub. No.: WO2012/131394
PCT Pub. Date: Oct. 4, 2012

(65) Prior Publication Data
US 2014/0051599 A1    Feb. 20, 2014

(30) Foreign Application Priority Data

Mar. 31, 2011  (GB) .................................. 1105436.8

(51) Int. Cl.
| | | |
|---|---|---|
| *G01N 33/53* | (2006.01) | |
| *A61K 39/04* | (2006.01) | |
| *A61K 39/02* | (2006.01) | |
| *G01N 33/569* | (2006.01) | |
| *G01N 33/58* | (2006.01) | |

(52) U.S. Cl.
CPC ........ *G01N 33/5695* (2013.01); *G01N 33/582* (2013.01); *G01N 2469/20* (2013.01)

(58) Field of Classification Search
CPC .... A61K 39/02; A61K 39/04; A61K 39/395; A61K 39/40
USPC ......... 424/130.1, 164.1, 184.1, 234.1, 248.1; 435/4, 7.1
See application file for complete search history.

(56) References Cited

U.S. PATENT DOCUMENTS

| | | | |
|---|---|---|---|
| 5,721,109 A | 2/1998 | Yano et al. | |
| 6,929,943 B1 | 8/2005 | Quapil et al. | |
| 7,384,793 B2 * | 6/2008 | McCash ................ | A61B 5/097 435/286.2 |
| 2009/0111125 A1 * | 4/2009 | Verschoor .......... | G01N 33/5695 435/7.21 |
| 2010/0279271 A1 | 11/2010 | McCash et al. | |

FOREIGN PATENT DOCUMENTS

| | | |
|---|---|---|
| EP | 1079226 A1 | 2/2001 |
| EP | 1371966 A1 | 12/2003 |
| EP | 1371967 A1 | 12/2003 |
| WO | 0114859 A1 | 3/2001 |
| WO | 2005116654 A1 | 12/2005 |
| WO | 2009130506 A2 | 10/2009 |
| WO | 2009130508 A1 | 10/2009 |
| WO | 2010086667 A2 | 8/2010 |

OTHER PUBLICATIONS

Patent Cooperation Treaty, International Preliminary Report on Patentability and Written Opinion of the International Searching Authority for PCT/GB2012/050726 dated Oct. 10, 2013, 7 pages.
Patent Cooperation Treaty, International Search Report and Written Opinion of the International Searching Authority for PCT/GB2012/050726 dated Jun. 15, 2012, 11 pages.
Lemmer et al., "Detection of Antimycolic Acid Antibodies by Liposomal Biosensors," 2009, 26 pages, Methods in Enzymology, vol. 464.

* cited by examiner

*Primary Examiner* — Rodney P Swartz
(74) *Attorney, Agent, or Firm* — Hoffman Warnick LLC

(57) ABSTRACT

A method of determining the presence or absence in a sample of a biomarker indicative of exposure to mycobacteria, the method comprising: (a) providing a substrate carrying a mycolic acid derived antigen; (b) contacting the substrate with the sample; (c) contacting the substrate with a fluorophore species; (d) creating an evanescent wave at the boundary of the substrate and the sample; (e) detecting the presence or absence of fluorescence.

10 Claims, 1 Drawing Sheet

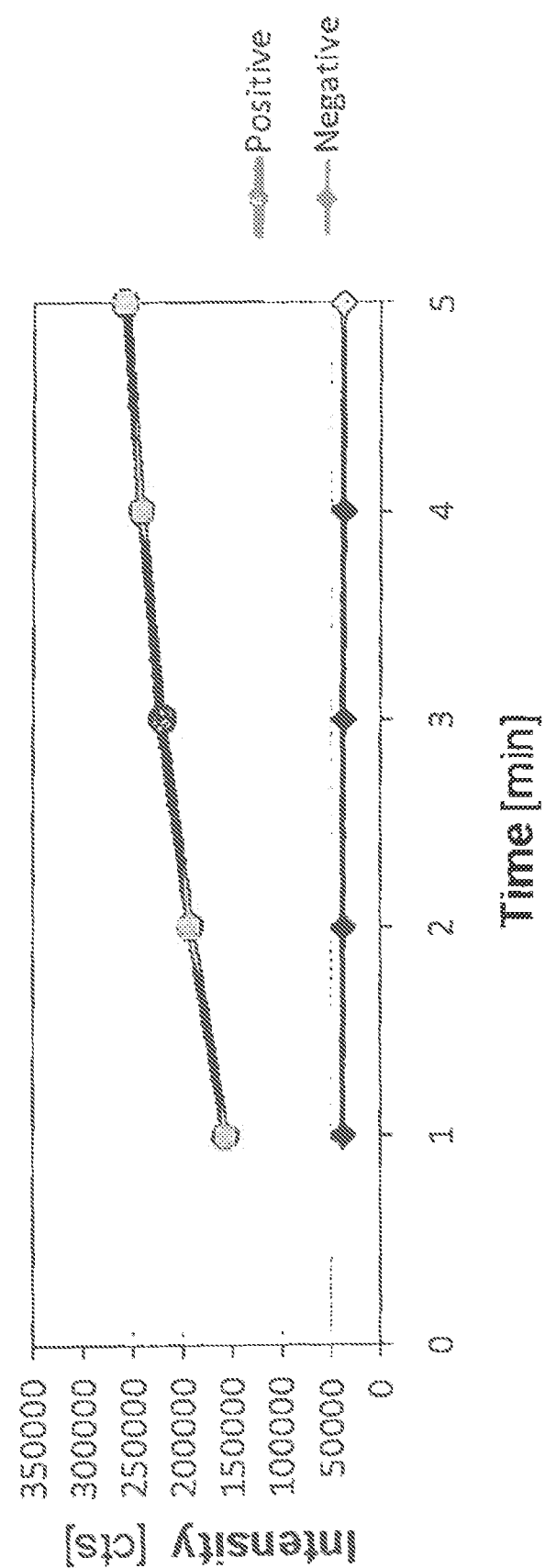

METHOD FOR DETERMINING EXPOSURE TO MYCOBACTERIA

The present invention relates to a kit and method for detecting an antibody in a sample. In particular the invention provides a quick method for determining whether or not an individual is infected with a mycobacterial disease.

Pathogenic and non-pathogenic mycobacteria are very widespread in the environment and their rapid detection and distinction represents an important public health target.

For example, tuberculosis is a serious and often fatal disease which affects humans and other animals and is caused by infection with mycobacteria. Infection with *Mycobacterium tuberculosis* is very common and it is estimated that up to a third of the world's population is infected with the bacterium. Most of those infected will never develop the active disease but because it is often fatal if left untreated, early diagnosis of the disease is essential. Methods of detecting *M. tuberculosis* are known but these existing methods have a number of disadvantages. It can often take a long time for the results of a test to be known, the equipment needed is expensive or difficult to use and the results are not always reliable. A number of serodiagnostic assays have been developed for the diagnosis of tuberculosis but none of these reach the standards required by the World Health Organisation.

Incidence of active tuberculosis disease is very common in certain areas of the world, especially where there is co-infection with HIV. The presence of HIV can suppress some of the indicators typically found in the blood of a patient infected with *M. tuberculosis*, leading to missed diagnoses.

Many existing techniques for use in detecting antibodies found in an individual infected with *M. tuberculosis* require a serum sample. This means that a blood sample must be treated before it can be tested. In many countries suitable facilities to treat the blood do not exist and where they do treatment of the blood sample to obtain serum increases the time and cost associated with obtaining a diagnosis. It would thus be desirable to provide a method by which whole blood could be tested.

The life expectancy of an individual co-infected with *M. tuberculosis* and HIV is often only a few weeks. Thus there exists an urgent need to provide a method by which infection with tuberculosis and other mycobacterial diseases can be detected quickly and reliably.

Infectious diseases, for example tuberculosis, cause a person or animal infected with the disease to produce antibodies. Identification of these antibodies in a sample taken from an infected individual can lead to a diagnosis of the disease.

According to a first aspect of the present invention there is provided a method of determining the presence or absence in a sample of a biomarker indicative of exposure to mycobacteria, the method comprising:
   (a) providing a substrate carrying a mycolic acid derived antigen;
   (b) contacting the substrate with the sample;
   (c) contacting the substrate with a fluorophore species;
   (d) creating an evanescent wave at the boundary of the substrate and the sample;
   (e) detecting the presence or absence of fluorescence.

BRIEF DESCRIPTION OF THE DRAWINGS

FIG. 1 shows variation with time of fluorescence emitted following contact of a substrate carrying antigen C with a serum sample known to be positive for tuberculosis, and a serum sample known to be negative for tuberculosis, using the procedure according to one aspect of the invention.

The present invention relates to a method of determining the presence or absence in a sample of a biomarker indicative of exposure to mycobacteria. By a biomarker we mean to refer to any molecule or combination of molecules that would be produced by a life form in response to exposure to mycobacteria. Such a life form may be a plant or animal. Preferably it is an animal. Most preferably the sample has been taken from a mammal.

The method of the present invention may be used to determine the presence or absence of a biomarker indicative of exposure to normally non-pathogenic or environmental mycobacteria. However in preferred embodiments the biomarker is indicative of infection with a mycobacterial disease. In such embodiments the biomarker is an antibody indicative of infection with the disease and may be further referred to herein as a "disease antibody".

The present invention therefore preferably relates to a method of determining the presence or absence in a sample of a disease antibody indicative of infection with a mycobacterial disease. The term "disease antibody" as used herein refers to an antibody produced by an individual infected with a disease. The infected individual may be an animal or a human.

The present invention may be used to determine the presence or absence of a disease antibody indicative of infection with any disease caused by infection with mycobacteria. Examples of such diseases include tuberculosis, leprosy, pulmonary disease, Buruli ulcer and bovine tuberculosis.

The present invention may also be used to determine the presence or absence of antibodies to lipids generated by exposure to non-pathogenic mycobacteria.

The invention finds particular utility in determining the presence or absence in a sample of disease antibodies indicative of the presence of tuberculosis. The sample may be taken from any animal suspected of infection with tuberculosis. Suitably the animal is a human.

Tuberculosis is a disease which is particularly prevalent in developing countries and many sufferers are also infected with HIV. However some of the current techniques used in the diagnosis of tuberculosis rely on the detection of a protein antibody. Antibodies against proteins may be suppressed in individuals who are HIV-positive.

The present invention involves contacting the sample with a substrate carrying a mycolic acid derived antigen. Such compounds are antigens for lipid antibodies generated by infection with mycobacteria. This is highly advantageous since, unlike protein antibodies, antibodies against lipids (which may be referred to herein as lipid antibodies) are not suppressed in individuals with compromised immune systems, for example those infected with HIV.

Step (a) of the present invention involves providing a substrate carrying a mycolic acid derived antigen. By the term "mycolic acid derived antigen" we mean to include mycolic acid compounds themselves and derivatives of mycolic acids, for example esters and/or salts thereof. Mycolic acids are characteristic components of the cell walls of mycobacteria and some related species.

Suitably the substrate provided in step (a) of the present invention may carry one or more antigens selected from one or more mycolic acids and/or one or more esters of mycolic acids. Suitable esters for use as antigens include glycerol esters and especially sugar esters. Preferred sugar esters of mycolic acids are trehalose monomycolates or trehalose dimycolates (also known as cord factors). Both cord factors and mycolic acids can be isolated as mixtures from natural sources.

Compounds isolated from natural sources may be used as the antigen carried on the substrate. Alternatively and/or additionally synthetically prepared compounds may be carried on the substrate. An advantage of using synthetic compounds is that they may be prepared in highly purified form and thus the specificity for a particular antibody can be improved.

Suitable synthetically prepared mycolic acid derived compounds for use herein as antigens include the mycolic acid compounds described in WO2009/130506, WO2009/130508 and the sugar esters described in WO 2010/086667.

As is shown by way of example in formula I, two moieties can be distinguished in each mycolic acid: the main branch, or meromycolate moiety, and the mycolic motif, an α-alkyl β-hydroxy acid. The structure of the mycolic motif is common to each naturally occurring mycolic acid, except for minor variations in the length of the chain in the α-position. The two stereocentres in the α and β positions relative to the carboxylic group present in all natural mycolic acids have, when examined, always been found to both be in the (R)-configuration in these natural products. On the other hand, the meromycolate section, which generally contains two functionalities and three long chains (a, b, c in formula I), can be differently substituted in both the proximal (the one nearer the hydroxy-acid) and the distal position (further from the carboxylic acid).

Formula I

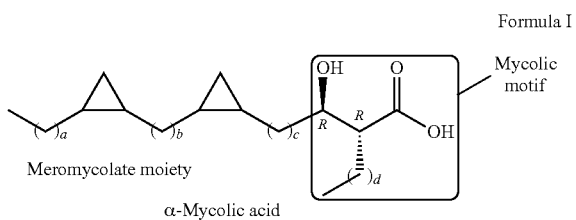

α-Mycolic acid

The mycolic acids are broadly separated into classes, according to the groups present in the meromycolate moiety. The proximal or distal functional groups can include cyclopropanes, double bonds, an epoxy group, a methoxy group, carbonyl group, carboxyl group or methyl group.

Suitable mycolic acid classes for use herein as antigens include keto mycolic acids having the structure shown in formula IIa; hydroxy mycolic acids having the structure shown in formula IIb; alpha mycolic acids having the structure shown in formula IIc; and methoxy mycolic acids having the structure shown in formula IId:

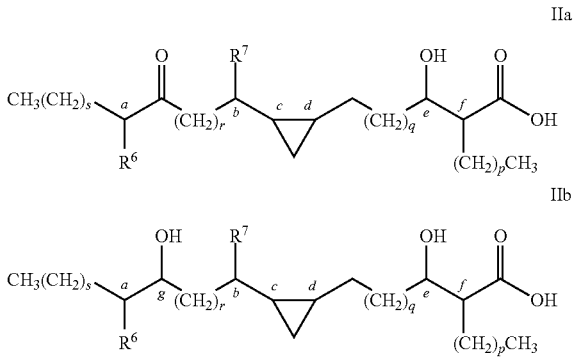

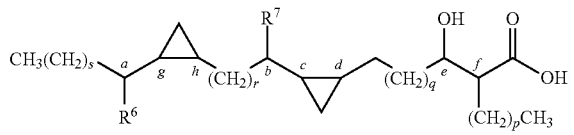

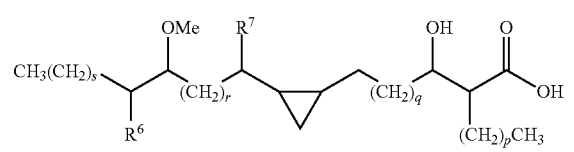

In each of the structures IIa, IIb, IIc and IId $R^6$ may be hydrogen or $C_1$ to $C_4$ alkyl. Preferably $R^6$ is hydrogen or methyl.

In each of the structures IIa, IIb, IIc and IId $R^7$ may be hydrogen or $C_1$ to $C_4$ alkyl. Preferably $R^7$ is hydrogen or methyl.

In each of the structures IIa, IIb, IIc and IId p is preferably from 4 to 40, preferably from 8 to 36, more preferably from 12 to 32, for example from 16 to 30, more preferably from 20 to 28, for example from 22 to 26.

In the structures IIa, IIb, IIc and IId q is preferably from 2 to 40, more preferably from 4 to 36, for example from 6 to 30, preferably from 8 to 24, for example from 10 to 20 and preferably from 12 to 18.

In the structures IIa, IIb, IIc and IId, r is preferably from 2 to 40, for example from 6 to 36, preferably from 10 to 32, for example from 12 to 28, and preferably from 14 to 24.

In the structures IIa, IIb, IIc and IId, s is preferably from 2 to 40, for example from 6 to 36, preferably from 10 to 32, for example from 12 to 28, and preferably from 14 to 24.

In the structures IIa, IIb, IIc and IId, each of the chiral centres indicated at a, b, c, d, e, f, g and h may independently have either an (R) or an (S) configuration. Each cyclopropyl group may have either absolute stereochemistry and may have a trans or a cis configuration.

Any of the stereocentres indicated by a, b, c, d, e, f, g or h may be racemic. In the case of structure IIa it is possible that the stereocentre designated a will be racemic as this is a readily epimerisable position.

In addition to the compounds illustrated by the structures IIa, IIb, IIc and IId, other classes of mycolic acids may be useful as antigens in the present invention. Further suitable classes of mycolic acid include those substituted with epoxy and alkene groups in the meromycolate moiety. The structure of such compounds will be known to the person skilled in the art.

As mentioned above the substrate provided in step (a) of the method of the present invention may carry one or more mycolic acids and/or may carry one or more esters or salts of mycolic acids.

Especially preferred esters are sugar esters, especially trehalose monomycolates and trehalose dimycolates. Trehalose dimycolates (or cord factors) have the structure shown in formula III wherein MA represents the residue of a mycolic acid:

Formula III

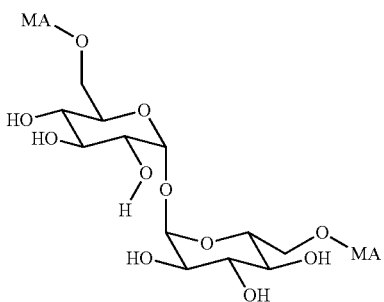

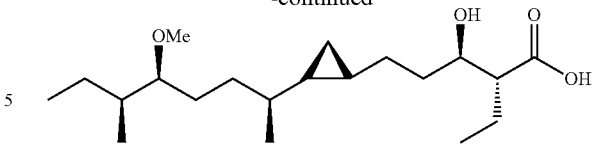

In formula III each MA residue may be of the same or a different mycolic acid.

In some embodiments the antigen comprises a keto mycolic acid.

In some embodiments the antigen comprises a hydroxy mycolic acid.

In some embodiments the antigen comprises a methoxy mycolic acid.

In some embodiments the antigen comprises an alpha mycolic acid.

Examples of suitable compounds which may be used as antigens in the present invention either alone or in combination are shown in formula IV:

Formula IV

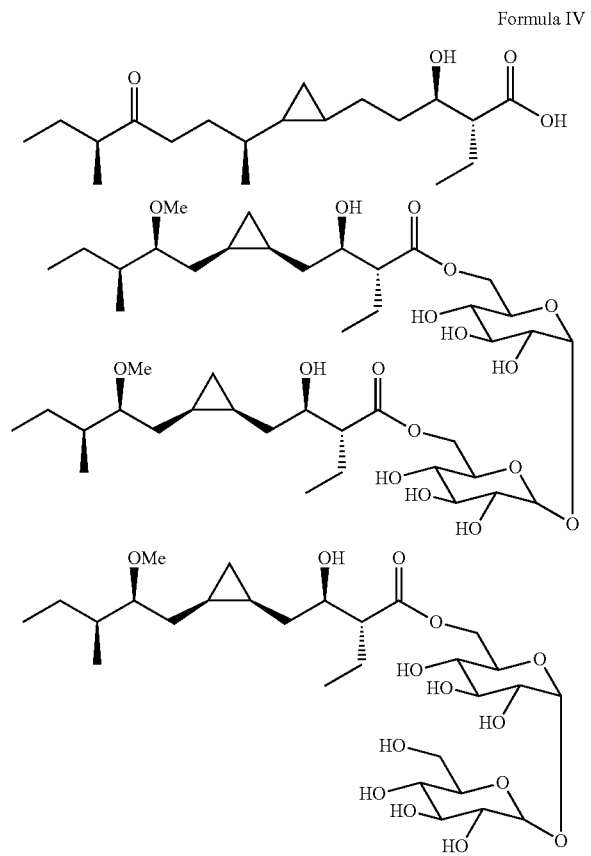

The substrate may be made from any suitable material and such materials will be well known to the person skilled in the art. For example the substrate may be made from a an organic or inorganic material for example a polymeric material, glass, a cellulosic material or a mixture thereof. In some embodiments the surface of the substrate may be pretreated to improve binding of the antigen, for example by irradiation with gamma rays or another suitable method. Suitably the substrate comprises an array of wells or cuvettes. These may be in the form of a linear array, a matrix-like array or any other suitable arrangement. Preferably the substrate is in the form of a microtitre plate (or a part thereof) comprising a plurality of wells. Suitably at least one well has one or more mycolic acid derived antigens carried on the bottom surface thereof. Other wells of the microtitre plate may also carry one or more mycolic acid derived antigens and/or may carry one or more other antigens and/or may be control wells in which no antigen is present. In embodiments in which one or more wells of the microtitre plate carries an antigen which is not mycolic acid derived, each such antigen may be an antigen for a disease antibody which is indicative of infection with a mycobacterial disease (for example a protein antibody) and/or may be indicative of infection with a different disease.

The or each antigen is carried on the substrate. By this we mean that the antigen has an affinity with the substrate and suitably forms an interaction therewith. This may be a covalent bond, a non-covalent bond, an electostatic interaction, an ionic force, hydrophobic interaction, absorption or a combination thereof. In the preparation of the substrate the antigen may be applied onto the substrate by any suitable means. Suitable physical and chemical means will be known to the person skilled in the art and include, for example deposition in a solvent followed by evaporation, chemical bonding or direct attachment to the surface via gold. In some embodiments the or each antigen is printed onto the substrate.

In some embodiments the antigen may be mixed with a diluent. Suitable diluents may be known to the person skilled in the art and include fatty acids, for example stearic acid.

In some embodiments of the present invention the substrate carries a plurality of antigens. Each antigen may bind to the same and/or different biomarkers, for example disease antibodies. In cases where the antigens bind to different disease antibodies these different antibodies may be indicative of the same and/or different diseases. Thus in some embodiments the present invention may be used to test for the presence of a plurality of antibodies indicative of a single disease whereby a particular combination of antibodies should be present in order to confirm the disease. Alternatively and/or additionally the present invention could be used to test for the presence of a plurality of antibodies each or some of which are indicative of different diseases.

In embodiments in which the substrate carries a plurality of antigens these may be located at substantially the same or different positions on the substrate. Suitably different antigens are located at different positions.

In some especially preferred embodiments in which the substrate comprises a microtitre plate each well contains only a single antigen. By this we mean that substantially all of the antigen present in one particular well is the same compound. Preferably only a single synthetic compound is present in any one well. Where a substrate comprises a plurality of different wells, the different wells may contain different antigens but it is preferred that only one compound is present in any single well. The use of a single synthetic compound as the antigen enables an accurate determination of a biomarker in the sample having a high specificity for that particular antigen. In some embodiments a plurality of wells may each contain different single antigen compounds. A particular combination may be selected to provide an accurate identification of exposure to a particular *mycobacterium*.

In step (b) of the method of the present invention the substrate is contacted with the sample.

Any suitable sample may be analysed using the present invention. Suitably the sample is selected from serum, blood, saliva, urine or sputum. In embodiments in which the sample is whole blood the method may include a step of first separating serum from the blood. This may be achieved, for example, by linking the substrate with a filter through which the blood must first flow before it reaches the assay. Other suitable methods will be known to the person skilled in the art.

However in some preferred embodiments the sample contacted with the substrate in step (b) of the method of the present invention is a whole blood sample. It is particular advantage of the invention that a whole blood sample may be tested directly as this reduces the time and cost to achieve a diagnosis of infection with a mycobacterial disease.

Step (c) of the method of the present invention involves contacting the substrate with a fluorophore species.

Steps (b) and (c) may be carried out in any order and may be carried out simultaneously or sequentially. Thus in some embodiments the substrate may be contacted with a fluorophore species and then contacted with the sample. In some embodiments the substrate may be contacted with the sample and then contacted with the fluorophore species. In some embodiments the substrate may be contacted with a composition comprising the sample and a fluorophore species. For example a fluorophore species may be added to the sample before it is contacted with the substrate. In some embodiments the fluorophore species may be carried on the substrate with the antigen. The fluorophore species may in some embodiments be part of the antigen molecule.

When the substrate is contacted with a sample which does contain a biomarker indicative of exposure to mycobacteria this biomarker becomes bound to or interacts with the mycolic acid derived antigen which is carried by the substrate. Thus the biomarker is held via the antigen at or very near to the surface of the substrate to form a biomarker—antigen complex.

When the fluorophore species is contacted with the biomarker—antigen complex this forms an interaction with the complex and thus the fluorophore species is also held at or very near to the surface of the substrate.

Any suitable fluorophore species can be used. For example the fluorophore species may be a secondary antibody which is able to interact with the biomarker (for example a disease antibody). Such a secondary antibody suitably includes a fluorescent moiety.

In some embodiments the fluorophore species may comprise the combination of a secondary antibody able to interact with the biomarker and a fluorescent dye molecule which is able to interact with the secondary antibody. Other suitable arrangements can be used as will be appreciated by the person skilled in the art.

Step (d) of the method of the present invention is suitably carried out after steps (a), (b) and (c) and involves creating an evanescent wave at the boundary of the substrate and the sample.

The evanescent wave is formed at the interface of the substrate and the sample. This is typically a solid liquid interface. An evanescent wave is one whose intensity decreases exponentially with distance from the boundary at which it is formed. As the skilled person will appreciate an evanescent wave is one which forms when a wave undergoes total internal reflection at a boundary as its angle of incidence is greater than the critical angle.

Thus the evanescent wave created in step (d) is suitably formed in the liquid sample by applying a wave of electromagnetic radiation to the other side of the solid substrate. This wave suitably passes through the solid material of the substrate but when it meets the boundary with the sample it undergoes total internal reflection and forms an evanescent wave.

Because the evanescent wave decays exponentially it exists for only a very short depth in the sample. Typically the penetration depth is less than the wavelength of the radiation used to form the evanescent wave, for example less than half its wavelength.

The evanescent wave is generated by total internal reflection (TIR). There are many ways to generate TIR and evanescent waves and these will be known to the person skilled in the art.

In a preferred embodiment an optical prism like structure is used to illuminate the bottom of the substrate using an angle of incidence greater than the critical angle. The critical angle $\theta_c$ is defined as $$\theta_c = \arcsin\left(\frac{n_{sam}}{n_{sub}}\right)$$

wherein $n_{sam}$ is the refractive index of the sample and $n_{sub}$ is the refractive index of the substrate. The critical angle may exist if $n_{sam} < n_{sub}$. The substrate is preferably transparent for the wavelength used to illuminate the substrate and/or for the wavelength at which photons are emitted by the fluorophore species.

The evanescent wave is suitably of a wavelength which excites the fluorophore species. It is suitably an electromagnetic wave. Any suitable wavelength may be used provided it is used in combination with an appropriate fluorophore.

Preferably the evanescent wave is selected from ultraviolet, visible or infrared light. Preferably it has a wavelength of from 200 to 2000 nm, preferably 400 to 900 nm, more preferably 500 to 700 nm.

The electromagnetic radiation applied to form the evanescent wave in step (d) may be applied by any suitable means. Such means will be known to the person skilled in the art. Suitable apparatus which could be used for this purpose is described in WO2001/014859, EP1371966, EP 1371967, EP 1079226 and EP 1204856.

Step (e) involves detecting the presence or absence of fluorescence, i.e. detecting photons emitted from the fluorophore species. This fluorescence occurs due to the creation of the evanescent wave in step (d). Because it decays exponentially the evanescent wave does not penetrate into the bulk of the sample and thus only excites any fluorophore species which are present at or very near to the surface of the substrate. A high concentration of fluorophore species will only be present at the surface if these have formed an interaction with the biomarker—antigen complex. Thus if fluorescence is observed this is an indication that the sample contains a biomarker indicative of exposure to mycobacteria.

Thus if fluorescence is observed in step (e) this is an indication that the sample contains a biomarker indicative of exposure to mycobacteria, for example a disease antibody indicative of infection with a mycobacterial disease. If no fluorescence is observed in step (e) this is an indication that the sample does not contain a biomarker indicative of exposure to mycobacteria, for example a disease antibody indicative of infection with a mycobacterial disease.

In some embodiments step (e) may involve quantitatively measuring the fluorescence emitted at a particular portion of the substrate. In embodiments in which the substrate comprises a plurality of different antigens located at different positions, for example a microtitre plate comprising a plurality of wells having different antigens in each well, step (e) may involve measuring the extent of the fluorescence at each position. Comparative analysis of the intensity of the signal may allow for increased accuracy when determining the type of mycobacteria present in the same. Quantitative analysis of this type may also help determine the severity of infection with a mycobacterial disease.

In some parts of the world exposure to mycobacteria is very common and thus many humans and other animals living in these areas will produce antibodies to mycobacterial antigens even if they are not infected with an active disease, for example active tuberculosis. This can lead to difficulty in providing a positive diagnosis of a particular disease. The present invention allows the response to single antigens and particular defined combinations thereof to be determined and if necessary in a quantitative manner. It therefore provides a more reliable and accurate assessment of the presence or absence of specific disease antibodies known to be indicators of infection with a mycobacterial disease.

Step (e) may also involve measuring the intensity of fluorescence over time. This information may also be useful in determining the type or extent of infection with a mycobacterial disease.

In some embodiments step (e) may involve simply visually observing the presence or absence of fluorescence at one or more positions on the substrate to provide a qualitative assessment. In other embodiments step (e) may involve quantitative measurement of the intensity of fluorescence at one or more positions on the substrate and at one or more points in time. In some embodiments fluorescence may be measured continuously over a period of time. Thus step(e) of the method of present invention may involve measuring the rate of change of intensity of fluorescence with time.

Quantitative measurement of the intensity of fluorescence may be carried out by any suitable means. A suitable detection unit can be used for the detection of photons emitted from the fluorophore species. A detection unit may comprise a light collection optics, optical filters and an optical detector. The light collection optics is preferably a set of optical lenses that efficiently collect the photons emitted by the fluorophore species and direct them onto the optical detector. The optical filters are able to select the photons emitted by the fluorophore species by one or more properties, for example wavelength, polarisation, intensity and propagation direction.

In preferred embodiments a wavelength selective filter is used that blocks the excitation wavelength and is transparent for the emitted photons. Suitable optical detectors will be known to the person skilled in the art and include a camera, photodiode and light sensitive film.

Suitably where the intensity of fluorescence is quantitatively measured at a plurality of positions on the substrate at one or more points in time this data may be recorded using a computer. Such a computer could then be used to compare new samples with data from previous samples to increase the accuracy and specificity of identification of particular antibody combinations indicative of infection with a mycobacterial disease.

When used to analyse known samples of sera from individuals some of whom had been infected with *M. tuberculosis*, the method of the present invention was found to provide a greater degree of discrimination between positive and negative samples compared with using standard methods based on ELISA assays.

When the method of the present invention is used to test for disease antibodies indicative of infection with a mycobacterial disease it can provide results quickly, with improved accuracy, using whole blood samples and at moderate cost. It therefore provides significant advantages over the prior art.

In a second aspect the present invention may further provide a kit for use in the method of the first aspect.

In a third aspect the present invention may further provide a substrate for use in the method of the first aspect.

The invention will now be further described with reference to the following non-limiting examples.

EXAMPLE 1

The following synthetic antigen compounds were prepared as single compounds (having a purity of greater than 95%) using methods described in or analogous to those described in WO2009/130508, WO2009/130506 and WO 2010/086667:

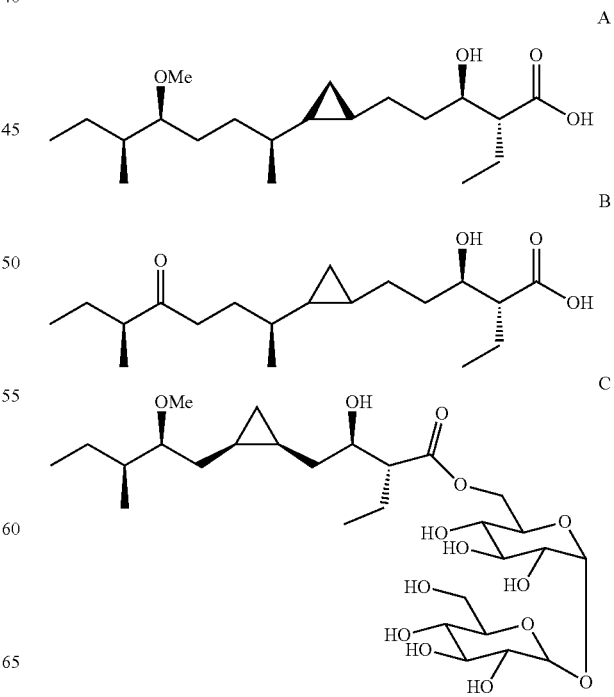

-continued

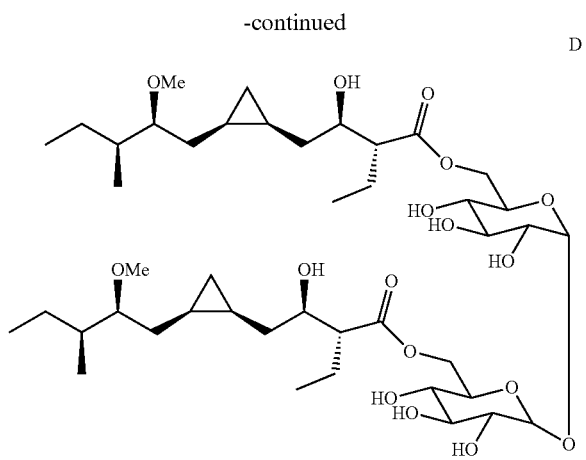

D

EXAMPLE 2

Buffers and Solutions were Made Up as Follows:
PBS (Phosphate Buffered Saline) Stock Solution:
20×PBS stock solution was prepared by dissolving NaCl (160 g), KCl (4 g), $KH_2PO_4$ (4 g) and $Na_2HPO_4$ (23 g) in 900 ml of ultra-pure double distilled de-ionised water ($dddH_2O$). The solution was made up to a final volume of 1 L using $dddH_2O$ and filtered through a 0.22 µl membrane filter.
1×PBS Buffer:
Dissolve 50 ml of the 20×PBS stock solution in 950 ml $dddH_2O$. The pH was checked to be 7.4.
0.5% Casein/PBS Buffer:
20×PBS stock solution (50 ml) was added to 700 ml $dddH_2O$ in a liter flask. Casein (5 g) (carbohydrate and acid free) was added to this solution and dissolved by stirring at 37° C. for 2 hours. The solution was stored overnight at 4° C., and the pH adjusted to 7.4 on the following day using NaOH (1 M) before being made up to a final volume of 1 L.
Goat Anti-Bovine IgG Peroxidise Conjugate:
10 µl of the peroxidise conjugate was added to 10 ml of 0.5% Casein/PBS. This solution was only prepared 5 minutes before use.
0.1 M Citrate Buffer:
0.1 M citric acid (450 ml) was added to a 0.1 M tri-sodium citrate solution (450 ml) until the pH was 4.5. The volume was made up to 1 L using $dddH_2O$.
O-Phenylenediamine Dihydrochloride (OPD) Substrate:
OPD (10 mg) and $H_2O_2$ (8 mg) was added to 0.1 M citrate buffer (10 ml). The substrate was prepared 5 minutes prior to use.

EXAMPLE 3

Antigens were applied to a multi-well microtitre substrate and contacted with sample and a fluorophore species as follows:
Antigens were dissolved in hexane to give an antigen solution of concentration 60 µg/ml. 25 µl of this solution was added to each well, and the solvent was left to evaporate at room temperature overnight. 80 µl of 0.5% casein/PBS buffer (pH=7.4) was added to each well, and incubated at room temperature for 15 minutes. The buffer was removed and any excess buffer was flicked out until the plates were dry. Serum samples were diluted to a concentration of 1:20 in casein/PBS buffer and was added to each well (25 µl) and incubated for 30 minutes. The substrate plates were washed with casein/PBS buffer 3 times and any excess buffer was flicked out onto a paper towel until dry. 20 µl of a secondary antibody solution (containing a fluorophore species) made up of goat anti-human IgG APC F(ab')$_2$ fragment specific (1 µg) and BBN (0.4 µg) in casein/PBS buffer (1 ml) was added to each well.
Immediately after addition of the serum sample and fluorophore species to the substrate, an infrared wave (of wavelength 635 nm) was applied to the underside of the substrate at an angle greater than the critical angle to create an evanescent wave at the boundary of the substrate and the sample. Measurements of the intensity of the fluorescence at 492 nm were started immediately and recorded over a period of 5 minutes. The rate of change of intensity of fluorescence with time was recorded. This enabled any background fluorescence to be eliminated. The radiation was applied and the measurement of fluorescent recorded using an Evasensor EVA Reader apparatus. Arrays are based on classical optical arrangements and methods. An apparatus of this type is described in WO2001/014859.

EXAMPLE 4

Comparative

ELISA assays were carried out on some of the antigens to allow a comparison with the method of the invention, using the following procedure:
ELISA was carried out on 96-well micro-plates. Antigens were dissolved in hexane to give an antigen solution of concentration 60 µg/ml. 50 µl of this solution was added to each well, and the solvent was left to evaporate at room temperature for 2 hours before the plates were stored at 4° C. overnight in a plastic bag. Blocking was done by adding 400 µl of 0.5% casein/PBS buffer (pH=7.4) to each well, and incubated at 25° C. for 2 hours. The buffer was removed and any excess buffer was flicked out until the plates were dry. Serum was diluted to a concentration of 1:20 in casein/PBS buffer and was added to each well (50 µl) and incubated at 25° C. for 1 hour. The plates were washed with 400 µl casein/PBS buffer 3 times using an automatic washer, and any excess buffer was flicked out onto a paper towel until dry. To each well, 50 µl of anti-human IgG (whole molecule or Fc specific) peroxidise conjugate secondary antibody (diluted to a concentration of 1:1000 in casein/PBS buffer) was added, and incubated at 25° C. for 30 minutes. The plates were again washed 3 times with 400 µl casein/PBS buffer using an automatic washer, and any excess buffer was again flicked out. 50 µl of the o-phenylenediamine substrate was added to each well, and incubated for 30 minutes at 25° C. The colour reaction was terminated by adding 50 µl of 2.5 M $H_2SO_4$, and the absorbance was read at 492 nm.

EXAMPLE 5

FIG. 1 shows the variation with time of the fluorescence emitted at 492 nm following contact of a substrate carrying antigen C with a serum sample known to be positive for tuberculosis, and a serum sample known to be negative for tuberculosis, using the procedure of example 3.

EXAMPLE 6

The method of the present invention was used to test sera samples known to positive for tuberculosis and sera samples known to be negative for tuberculosis, using the procedure outlined in example 3 for each of antigens A, B, C and D. The intensity measurements in table 1 were recorded after 5 minutes.

As a comparison the same samples and antigens were also tested using an ELISA assay following the procedure outlined in example 4.

The fluorescence in the evanescent field assay and the absorbance in the ELISA assay were each measured at 492 nm. The results are shown in table 1.

TABLE 1

| Antigen | Evasensor intensity measurement (cts, counts per second (photons)) | | ELISA absorbance measurements (relative units, log scale) | |
|---|---|---|---|---|
| | TB positive | TB negative | TB positive | TB negative |
| A | 31513 | 4038 | 3.25 | 0.65 |
| B | 7910 | −480 | 0.41 | 0.42 |
| C | 915312 | −761 | 3.40 | 0.35 |
| D | 409198 | 1321 | 3.25 | 0.75 |

The invention claimed is:

1. A method of determining the presence or absence in a sample of a biomarker indicative of exposure to mycobacteria, the method comprising:
   (a) providing a substrate carrying at least one mycolic acid derived antigen selected from one or more mycolic acids and one or more esters or salts of mycolic acids;
   (b) contacting the substrate with the sample;
   (c) contacting the substrate with a fluorophore species;
   (d) creating an evanescent wave at the boundary of the substrate and the sample; and
   (e) detecting a presence or an absence of fluorescence,
   wherein the fluorophore species is selected from a group consisting of: a secondary antibody able to interact with the biomarker and includes a fluorescent moiety, and a combination of a secondary antibody able to interact with the biomarker and a fluorescent dye molecule able to interact with the secondary antibody.

2. A method according to claim 1, wherein the substrate provided in step (a) carries a plurality of antigens, of which the at least one mycolic acid derived antigen comprises at least one.

3. A method according to claim 1, wherein the sample is a whole blood sample.

4. A method according to claim 2, wherein the substrate comprises a microtitre plate having a plurality of wells and each well contains a single synthetic antigen compound from among the plurality of antigens and at least one well contains the at least one mycolic acid derived antigen.

5. A method according to claim 1, wherein the evanescent wave has a wavelength of 400 to 900 nm.

6. A method according to claim 1, wherein step (e) includes visually observing the presence or absence of fluorescence at one or more positions on the substrate to provide a qualitative assessment.

7. A method according to claim 1, wherein step (e) includes quantitative measurement of an intensity of fluorescence at one or more positions on the substrate and at one or more points in time.

8. A kit for determining the presence or absence in a sample of a biomarker indicative of exposure to mycobacteria, the kit comprising a substrate carrying a mycolic acid derived antigen, a quantity of a fluorophore species, and instructions for carrying out a detection method comprising:
   (a) providing a substrate carrying a mycolic acid derived antigen;
   (b) contacting the substrate with the sample;
   (c) contacting the substrate with a fluorophore species;
   (d) creating an evanescent wave at the boundary of the substrate and the sample; and
   (e) detecting a presence or an absence of fluorescence,
   wherein the mycolic acid derived antigen is selected from a group consisting of: mycolic acids, glycerol esters of mycolic acids, and sugar esters of mycolic acids.

9. A substrate carrying a plurality of different mycolic acid derived antigens located at different positions on the substrate,
   wherein each of the plurality of different mycolic acid derived antigens is independently selected from a group consisting of: mycolic acids, glycerol esters of mycolic acids, and sugar esters of mycolic acids.

10. A substrate comprising a microtitre plate having a plurality of wells, each well containing a single synthetic antigen compound, and at least one of the plurality of wells containing a synthetic mycolic acid derived antigen selected from a group consisting of: mycolic acids, glycerol esters of mycolic acids, and sugar esters of mycolic acids.

* * * * *